ID [19]

United States Patent
Isogai et al.

[11] 4,308,054
[45] Dec. 29, 1981

[54] N-(2,6-DISUBSTITUTED-4-PYRIDYL)-N'-PHENYLUREAS

[76] Inventors: Yo Isogai, 1-2-609, Kamiyoga 1-chome, Setagayaku, Tokyo; Soshiro Takahashi, 904-10 A-415, Oaza Kamiokubo, Urawashi, Saitamaken; Koichi Shudo, 2000-10-2-116, Kosugayacho, Totsukaku, Kohokuku, Yokohamashi, Kanagawa; Toshihiko Okamoto, 7-19, Shinoharakita 1-chome, Kohokuku, Yokohamashi, Kanagawa, all of Japan

[21] Appl. No.: 200,352

[22] Filed: Oct. 24, 1980

[30] Foreign Application Priority Data

Nov. 2, 1979 [DE] Fed. Rep. of Germany ....... 7910428
Apr. 15, 1980 [JP] Japan ................................... 55/50209

[51] Int. Cl.$^3$ .................... A01N 47/30; C07D 213/75
[52] U.S. Cl. ....................................... 71/94; 546/292; 546/305; 546/306
[58] Field of Search ....................... 546/305, 306, 292; 71/94

[56] References Cited

U.S. PATENT DOCUMENTS 4,193,788  3/1980  Shudo et al. ........................ 546/306

FOREIGN PATENT DOCUMENTS 1122662  8/1968  United Kingdom .

Primary Examiner—Henry R. Jiles
Assistant Examiner—Bernard Dentz
Attorney, Agent, or Firm—Sughrue, Mion, Zinn, Macpeak and Seas

[57] ABSTRACT

N-(2,6-disubstituted 4-pyridyl)-N'-phenylurea compounds are plant growth regulators having potent cytokinin activity. N-(2,6-dichloro-4-pyridyl)-N'-phenylurea is useful for regulating plant growth.

8 Claims, 1 Drawing Figure

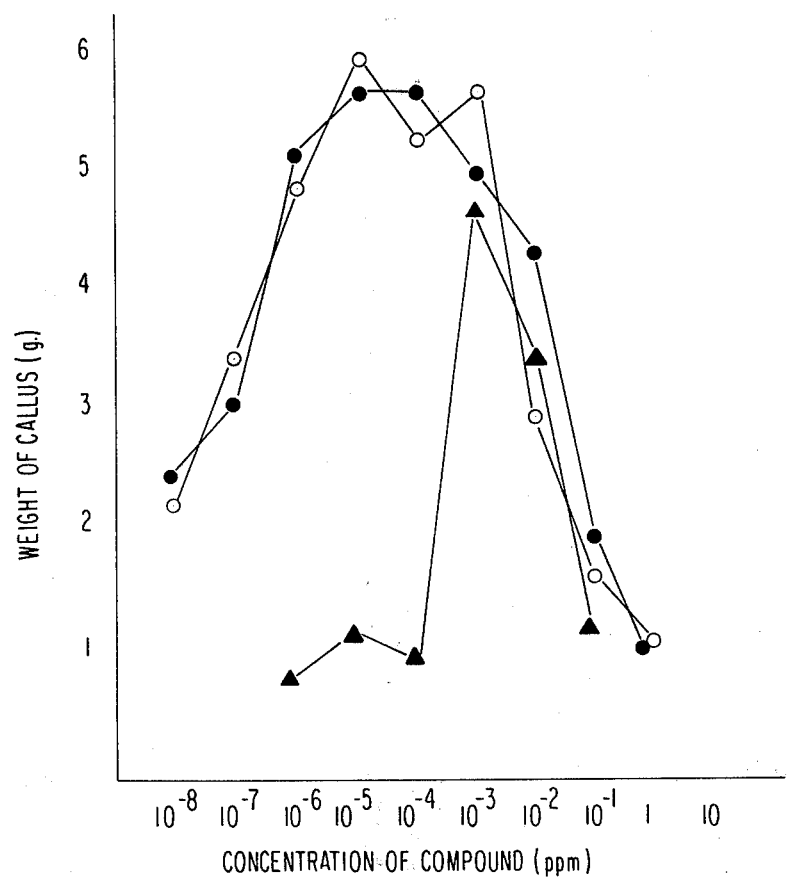

N-(2,6-DISUBSTITUTED-4-PYRIDYL)-N'-PHENYLUREAS

BACKGROUND OF THE INVENTION

1. Field of the Invention

This invention relates to novel N-(2,6-disubstituted 4-pyridyl)phenylureas and phenylthioureas, agricultural composition comprising such active ingredients and methods of treating plants therewith.

2. Brief Description of the Prior Art

In our co-pending application, Ser. No. 947,468 filed Oct. 2, 1978, now U.S. Pat. No. 4,193,788 it is disclosed that N-(2-chloro-4-pyridyl)-N'-phenyl ureas accelerate or retard plant growth when used in very small amounts in the agricultural and horticultural fields and are very useful as so-called plant growth regulators which control growth of plants. These urea compounds are specifically grouped into substances collectively referred to as cytokinin-like substances represented by $^6$N-benzyladenine, kinetin, N-(4-pyridyl)-N'-phenylurea, etc.

Plant growth regulators exhibiting cytokinin-like hormonal activity (hereafter referred to as cytokinin hormone activity) can accelerate plant growth when used in very small amounts. On the other hand, plant growth can sometimes be suppressed when such chemicals are employed in excess amounts, i.e., in amounts over that effective to accelerate plant growth (sometimes referred to as overdose use).

Accordingly, while the terms "plant growth regulation" and "plant growth regulator" used herein refer primarily to acceleration, they sometimes refer to suppression of plant growth (in overdose use) in a broad sense. Such seemingly contrary activities by the plant growth regulator are characteristic of cytokinin activity. In this regard, herbicides for which cytokinin activity has clearly been established are not known, though some herbicides have been shown to have auxin activity.

In addition to the above-described aromatic urea compounds, biological activities of N-(2-substituted-4-pyridyl)-N'-phenylurea compounds have been investigated by the present inventors (Ser. No. 62,850 filed Aug. 1, 1979 now U.S. Pat. No. 4,279,639). As a result, it has been found that requirements in chemical structure for exhibiting cytokinin activity reside in the N-(4-pyridyl) moiety, N'-phenyl moiety and the pyridine ring substituted with specific substituents such as a halogen atom, a methoxy group, an amino group, a cyano group, a trifluoromethyl group or the like at the 2-position thereof, in addition to the requirement that plant growth regulators be derived from urea or thiourea. Previous understanding was that 2,6-disubstituted compounds would cause a reduction in activity due to their steric hindrance since it has been heretofore established that compounds having the 2-alkyl-substituted pyridine moiety show activity only equivalent to compounds having no substituents thereon and further that 2,6-dialkyl-substituted compounds provide markedly reduced cytokinin activity.

On the other hand, the inventors have found, during the course of developing a more practical process for preparing N-(2-chloro-4-pyridyl)-N'-phenylurea, that N-(2,6-dichloro-4-pyridyl)-N'-phenylurea which was believed to be useful as an intermediate for the synthesis of a series of plant growth regulators discovered by the inventors shows unexpectedly potent cytokinin activity, notwithstanding the fact that the latter is disubstituted at the 2- and 6-positions thereof.

SUMMARY OF THE INVENTION

Accordingly, an object of this invention is to provide N-(2,6-disubstituted 4-pyridyl)-N'-phenylureas and -thioureas represented by formula:

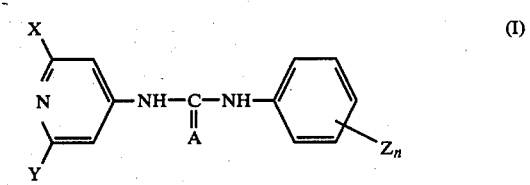

wherein X and Y, each of which may be the same or different, represents F, Cl, Br, CF$_3$, OR or SR wherein R represents a lower alkyl group; Z represents F, Cl, Br or a hydrogen atom; A represents an oxygen or sulfur atom; and n is 1 or 2. This invention also relates to a plant growth regulator comprising such active ingredients and methods of treating plants therewith.

BRIEF DESCRIPTION OF THE DRAWING

The Figure is a graph showing superiority of this invention in cytokinin activity to N-(2-chloro-4-pyridyl)-N'-phenylurea, in which callus yield (g.) is expressed on the y-axis and concentration (ppm) of phenylurea derivatives used on the x-axis.

DETAILED DESCRIPTION OF THE INVENTION

The N-(2,6-disubstituted 4-pyridyl)-N'-phenylureas and thioureas (hereafter often referred to collectively as "pyridylureas") of formula (I) of this invention provide excellent physiological activities on plants similar to the effects provided by benzyl adenine, but exhibit such effects when used in a much smaller amount.

More specifically, the compounds of this invention can accelerate plant growth, cell mitosis, cell enlargement, cell differentiation, fruit bearing, flowering or fruiting or can cause such effects to occur at a desired time; regulate growth of plants at a desired level; prevent fruit from falling; prevent or control ingredients (e.g., sugar, alkaloids) of fruit or sugar cane; improve the taste of edible plants, etc.

By adjusting the amount of the compounds of this invention employed, usually in the use of an overdose thereof, the compounds of this invention can conversely suppress plant growth to a desired level, with suppression of plant growth to an excessive degree generally being termed a herbicidal effect.

Thus, the plant growth regulators of this invention have a wide variety of practical features, e.g., not only can they promote or suppress plant growth but they also insure flowering or fruiting at a desired time, the formation of seedless fruit, maintain seeds in a dormant state or arouse seeds from a dormant state, prevent flowering or fruit plants and trees from shedding and prevent leaves from defoliating or accelerate leaf-defoliation.

It has now been found that such activities are particularly potent with compounds having substituents at the 2- and 6-positions of the pyridine nucleus, such as a halogen atom (preferably Cl, F, Br), CF$_3$, CN, OCH$_3$, etc., which inductively attract electrons; whereas compounds having strong polarity such as OH, NH$_2$, etc., have relatively weak activities; in addition, with respect to the phenyl nucleus of formula (I), compounds wherein Z represents a hydrogen atom or a halogen atom(s) (1 or 2), especially Cl or F, at the m-position thereof are particularly preferred.

Specific examples of the phenylurea compounds of formula (I) include N-(2,6-dichloro-4-pyridyl)-N'-phenylurea, N-(2,6-dichloro-4-pyridyl)-N'-m-fluorophenylurea, N-(2,6-dibromo-4-pyridyl)-N'-phenylurea, N-(2-chloro-6-methoxy-4-pyridyl)-N'-phenylurea, N-(2,6-dimethoxy-4-pyridyl)-N'-phenylurea, N-(2-chloro-6-methoxy-4-pyridyl)-N'-m-fluorophenylurea, etc.

The compounds of this invention can be prepared in a conventional manner. That is, the corresponding anilines of formula (II):

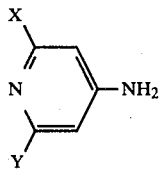

are reacted with isocyanates of formula (III):

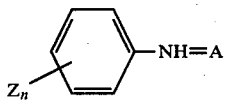

in an inert solvent such as benzene, tetrahydrofuran, acetonitrile, etc., at temperatures between room temperature and about 150° C. under normal pressure.

The starting material (II) can be prepared by reduction of the corresponding nitro compounds, or from 2,6-disubstituted isonicotinic acids through a Hoffmann rearrangement (via the corresponding amides) or through a Curtius rearrangement (via the corresponding hydrazides and then acid azides). The 2,6-disubstituted isonicotinic acids can easily be prepared by halogenation of citrazinic acid using $POCl_3$ or $POBr_3$.

Alternatively, the compounds of formula (I) can be prepared by the reaction of:

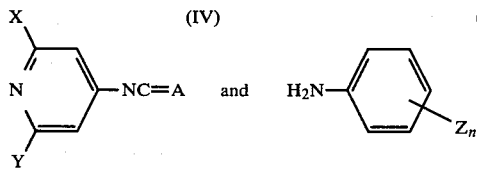

under reaction conditions similar to those in the reaction of (II) and (III) above. Further, a conventional process for preparing substituted ureas can also be used for the preparation of compounds (I).

The amount of the compounds of this invention used when applied by directly spraying plants is generally 10 to 100 liters per 10 ares as a solution of a concentration of 0.01 ppm to 1% as effective ingredient, preferably 0.1 ppm to 0.1%. When applied to the soil, an amount 5 to 10 times that given above is required. It goes without saying, however, that the amount applied will differ according to the object of the control and the plant to which the same is applied (e.g., far smaller concentrations ($\leq 0.0001$ ppm) in tissue culture). The compounds of this invention can be used alone or in admixture with other substances or compositions having effects desired during use, for example, other plant regulators, herbicides, insecticides, fungicides, and acaricides, typically in the form of solutions, emulsions, wettable powders, granules, fine granules, or powders.

The preparation of a suitable composition can be carried out in a conventional manner, e.g., by mixing 0.1 to 50%, preferably 0.1 to 10%, of a compound or compounds of this invention with a bulking agent, such as a liquid or solid diluent or carrier and, if desired or necessary, an emulsifying agent or dispersing agent.

Preferred liquid diluents or carriers include water, aromatic hydrocarbons such as xylene, benzene, and methylnaphthalene, chlorinated aromatic hydrocarbons such as chlorobenzene, mineral oil fractions such as paraffin, alcohols such as methanol and propanol, and polar solvents such as dimethyl formamide and acetone.

Preferred solid diluents or carriers include, for example, talc, clay, kaolin, white carbon, wood powder and sand.

Preferred emulsifying agents include polyoxyethylene-fatty acid esters or polyoxyethylene-fatty acid alcohol ethers and preferred dispersing agents include alkyl sulfonates, alkyl aryl sulfonates, alkali metal salts, alkaline earth metal salts, the ammonium salt of ligninsulfonic acid, and methyl cellulose.

The compounds of this invention or preparations thereof per se may be added to a medium or applied directly to the plant or onto the surface of leaves or stalks thereof, or sprayed on the soil; they are usually applied in the form of a conventional preparation thereof. Further, the plant growth controlling agents of this invention may be applied together with conventional fertilizers and/or extenders.

The compounds of this invention can also be used in the form of an inorganic or organic salt thereof such as the hydrochloride, phosphate, or sulfate, citrate or tartarate thereof.

The present invention will now be described in detail with reference to the examples below, but it is not to be deemed limited thereto.

The following Examples 1 to 5 show typical synthesis procedures for forming compounds of the present invention. Unless otherwise indicated, processing was at room temperature and at atmospheric pressure.

EXAMPLE 1

Preparation of N-(2,6-Dichloro-4-pyridyl)-N'-phenylurea

In 6 ml. of dry toluene, 114 mg. of 2,6-dichloroisonicotinic acid azide obtained by diazotizing 2,6-dichloroisonicotinic acid hydrazide was dissolved. To the resulting solution, 49 mg. of aniline was added and the mixture was heated at 100° C. for 3 hrs. with stirring. After cooling, crystalline N-(2,6-dichloro-4-pyridyl)-N'-phenylurea formed was taken out by filtration. The thus obtained crystals were almost pure, but completely pure product was obtained by silica gel chromatography in an amount of 125 mg. Yield 85%, m.p. 219°–222° C.

Analysis as $C_{12}H_9Cl_2N_3O$: Calcd. C: 51.09, H: 3.22, N: 14.89. Found. C: 51.31, H: 3.24, N: 14.65.

The product can also be prepared in good yield by heating the isonicotinic azide in an inert solvent such as toluene, etc. to prepare 2,6-dichloro-4-pyridyl isocyanate and then adding aniline to the resulting solution.

EXAMPLE 2

Preparation of N-(2,6-Dichloro-4-pyridyl)-N'-m-fluorophenylurea

In a manner similar to Example 1, N-(2,6-dichloro-4-pyridyl)-N'-m-fluorophenylurea showing a m.p. of 185°–188° C. was obtained except that m-fluoroaniline was used instead of aniline.

EXAMPLE 3

Preparation of N-(2,6-Dibromo-4-pyridyl)-N'-phenylurea

In a manner similar to Example 1, 230 mg. of crystalline N-(2,6-dibromo-4-pyridyl)-N'-phenylurea was obtained except that 219 mg. of 2,6-dibromoisoicotinic acid azide was used and the reaction with an equimolar amount of aniline was carried out for 6 hrs. under reflux with heating. Yield 87%, m.p. 237°–239° C.

Analysis for $C_{12}H_9Br_2N_3O$: Calcd. C: 38.85, H: 2.44, N: 11.33. Found. C: 39.15, H: 2.47, N: 11.14.

EXAMPLE 4

Preparation of N-(2-Chloro-6-methoxy-4-pyridyl)-N'-phenylurea

In a manner similar to Example 1, 142 mg. of N-(2-chloro-6-methoxy-4-pyridyl)-N'-phenylurea was obtained except that 136 mg. of 2-chloro-6-methoxyisonicotinic acid azide was used and reacted with an equimolar amount of aniline for 6 hrs. with heating under reflux. Yield 80%, m.p. 161°–162° C.

Analysis for $C_{13}H_{12}ClN_3O_2$: Calcd. C: 56.23, H: 4.36, N: 15.13. Found C: 56.58, H: 4.39, N: 15.02.

Using 2-fluoroaniline instead of aniline, N-(2-methyl-6-methoxy-4-pyridyl)-N'-m-fluorophenylurea showing a m.p. of 181°–183° C. was obtained in a similar manner.

EXAMPLE 5

Preparation of N-(2,6-Dimethoxy-4-pyridyl)-N'-phenylurea

In a manner similar to Example 1, 174 mg. of N-(2,6-dimethoxy-4-pyridyl)-N'-phenylurea was obtained except that 162 mg. of 2,6-dimethoxyisonicotinic acid azide and 72 mg. of aniline were stirred at 100° C. for 24 hrs. Yield 82%, m.p. 190.5°–192° C.

Analysis for $C_{14}H_{15}N_3O_3$: Calcd. C: 61.53, H: 5.53, N: 15.38. Found C: 61.73, H: 5.56, N: 15.20.

EXAMPLE 6

Growth effect test of N-(2,6-dichloro-4-pyridyl)-N'-phenylurea on Tobacco Callus cells Tobacco callus was cultured in Murashige-Skoog medium containing 0.00001 to 0.1 ppm of N-(2,6-dichloro-4-pyridyl)-N-phenylurea and 2 ppm of indole acetic acid as an auxin for 30 days at 26° C. The final weight of fresh (not dried) callus is given in Table 1 below. The control was tobacco callus cultured in the Murashige-Skoog containing indoleacetic acid alone; otherwise the conditions were identical. For the purpose of a comparison, values obtained in a medium containing an optimal amount (0.01 ppm) of benzyl adenine are also given in Table 1. Values are an average of six samples.

TABLE 1

|  | Concentration (ppm) | Weight (g) |
| --- | --- | --- |
| Compound of Invention | 0.00001 | 1.9 |
| Compound of Invention | 0.0001 | 4.5 |
| Compound of Invention | 0.001 | 5.3 |
| Compound of Invention | 0.01 | 3.7 |
| Compound of Invention | 0.1 | 0.9 |
| Benzyl adenine | 0.01 | 4.2 |
| Control | — | 0.2 |

It can be clearly seen that the compound of the present invention provided a similar product yield at a concentration of about 1/100 of the concentration at which benzyl adenine provided the maximum product yield, i.e., 0.01 ppm, and its excellent activity is apparent. It can also be seen that product yield with the compound of the invention was far lower (inhibitory) at a high concentration (0.1 ppm) than the maximum product yield with benzyl adenine.

EXAMPLE 7

In a manner identical to Example 6, the tobacco callus growth test was performed except for using N-(2,6-dichloro-4-pyridyl)-N'-(m-fluorophenyl)urea. The results obtained are shown in Table 2 below.

TABLE 2

|  | Concentration (ppm) | Weight (g) |
| --- | --- | --- |
| Compound of Invention | 0.00000001 | 2.1 |
| Compound of Invention | 0.0000001 | 1.9 |
| Compound of Invention | 0.000001 | 2.8 |
| Compound of Invention | 0.00001 | 2.8 |
| Compound of Invention | 0.0001 | 4.7 |
| Compound of Invention | 0.001 | 5.9 |
| Compound of Invention | 0.01 | 3.6 |
| Compound of Invention | 0.1 | 0.9 |
| Benzyl adenine | 0.1 | 3.7 |
| Control | — | 0.2 |

The activity of the compound of this invention was seen with an optimal concentration of 0.001 to 0.0001 ppm. Further, even at a 1/10 to 1/1000 concentration, sufficient activity was recognized with the compound of this invention. It can thus be seen that the compound of this invention is the most potent compound as compared to known compounds.

EXAMPLE 8

Shoot Formation Test: Effect of N-(2-chloro-6-methoxy-4-pyridyl)-N'-(m-fluorophenyl)urea on pith tissue due to cell differentiation in stalks and leaves of tobacco callus Sections of tobacco pith tissue were inoculated in a Murashige-Skoog medium as used in Example 6 but containing no auxin and cultured for 30 days at room temperature. Then, the number of pith sections forming shoots was counted. For comparison, benzyl adenine was tested in a similar way.

The results obtained are shown in Table 3 below.

TABLE 3

| Concentration (ppm) | Shoot Formation Rate* |
| --- | --- |
| Compound of Invention: | |
| 0.00001 | 5/6 |
| 0.0001 | 5/6 |
| 0.001 | 6/6 |
| 0.01 | 6/6 |
| 0.1 | 6/6 |
| 1 | 6/6 |
| Benzyl adenine: | |

TABLE 3-continued

| Concentration (ppm) | Shoot Formation Rate* |
| --- | --- |
| 0.01 | 2/6 |
| 0.1 | 5/6 |
| 1 | 6/6 |
| Control (blank) | 0/6 |

*Number of pith section forming shoots/number of pith sections inoculated

It can be seen from the results above that the compound of this invention provides a similar shoot formation rate to that with benzyl adenine at a much lower concentration.

EXAMPLE 9

Inhibition of Flower Shedding of N-(2,6-dichloro-4-pyridyl)-N'-phenylurea in Grapes This experiment was carried out using grapevines (variety Delaware) transplanted outdoors.

The above-identified compound (1, 10 or 100 ppm) or benzyl adenine (100 ppm; for comparison) was added to an aqueous solution containing 100 ppm of gibberelline and recemose flowers were dipped in each solution at the time period most suitable for treating with gibberelline. Ten days after full bloom, the flowers were dipped in an aqueous solution containing 100 ppm of gibberelline alone. Grapes were harvested 53 days thereafter and the inhibition effect of flower shedding, i.e., weight of each cluster and number of berries on each cluster, was measured.

The results obtained are shown in Table 4 below.

TABLE 4

| | Gibberelline Alone (control) | Compound of Invention | | | Benzyl adenine 100 ppm |
| --- | --- | --- | --- | --- | --- |
| | | 1 ppm | 10 ppm | 100 ppm | |
| Weight of Berry Cluster (g.) | 108 | 155 | 170 | 139 | 130 |
| Number of Berries per Cluster (No.) | 85 | 127 | 136 | 140 | 128 |

EXAMPLE 10

Increase of Weight and Supression of Height in Datura Sunguinea using N-(2,6-Dichloro-4-pyridyl)-N'-phenylurea

*Datura Sunguinea* sp. (average height 8 cm.) plants were transplanted outdoors. When the average height of the plants reached 19 cm., an aqueous solution of the above-identified compound in concentrations as shown in Table 5 below was sprayed onto the plants in an amount of 15 ml. per plant. Four weeks later, the plants were harvested and the height of the plants and the total weight over the ground (stems and leave) measured.

Results are shown in Table 5 below wherein values are an average of five plants.

TABLE 5

| Compound | Cocentration (ppm) | Height (cm.) | Total Weight (g.) |
| --- | --- | --- | --- |
| Compound of Invention | 10 | 83 | 312 |
| | 50 | 81 | 346 |
| | 100 | 78 | 320 |
| Benzyl adenine | 500 | 87 | 280 |
| Control | — | 90 | 270 |

EXAMPLE 11

The cytokinin activity of N-(2,6-dibromo-4-pyridyl)-N'phenylurea and N-(2,6-dibromo-4-pyridyl)-N'-m-fluorophenylurea was examimed with tobacco callus cells in a manner similar to Example 6 (note, the comparative study was made simultaneously).

For comparison, N-(2-chloro-4-pyridyl)-N'-phenylurea disclosed in U.S. Pat. No. 4,193,788, which is one of the most potent compounds having mono-substitution at the 2-position of the pyridine nucleus and whose use was also discovered by the present inventors, was tested in a similar manner.

The results obtained are shown in the Figure.

From the results in FIG. 1, it can be seen that the N-(2,6-disubstituted 4-pyridyl)-N'-phenylureas in accordance with this invention exhibit more potent activity at a lower concentration, and further over a wider range of concentration, as compared to N-(2-mono-substituted 4-pyridyl)-N'-phenylurea.

While the invention has been described in detail and with reference to specific embodiments thereof, it will be apparent to one skilled in the art that various changes and modifications can be made therein without departing from the spirit and scope thereof.

What is claimed is:

1. An N-(2,6-disubstituted 4-pyridyl)-N'-phenylurea compound represented by the formula:

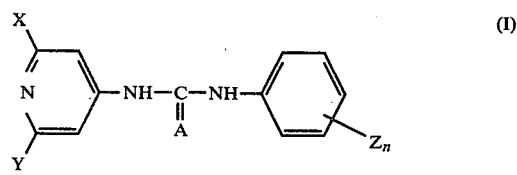

wherein X and Y, each of which may be the same or different, represents F, Cl, Br, CF$_3$, OR or SR wherein R represents a lower alkyl group; Z represents F, Cl, Br or a hydrogen atom; A represents an oxygen or sulfur atom; and n is 1 or 2.

2. The phenylurea compound of claim 1 wherein said X and Y, each of which may be the same or different, represents Cl, Br or CF$_3$, said Z represents F, and said A represents an oxygen atom.

3. N-(2,6-Dibromo-4-pyridyl)-N'-phenylurea.

4. N-(2,6-Dichloro-4-pyridyl)-N'-phenylurea.

5. N-(2,6-Dibromo-4-pyridyl)-N'-m-fluorophenylurea.

6. N-(2,6-Dichloro-4-pyridyl)-N'-m-fluorophenylurea.

7. An agricultural composition comprising an effective amount of a plant growth regulator comprising as an activeingredient a compound selected from the group consisting of an N-(2,6-disubstituted 4-pyridyl)-N'phenylurea compound of the formula:

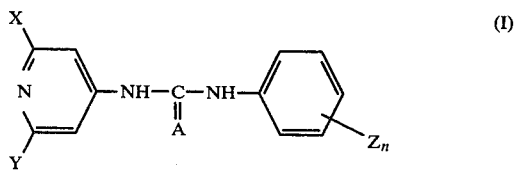

wherein X and Y, each of which may be the same or different, represents F, Cl, Br, CF3, OR or SR wherein R represents a lower alkyl group; Z represents F, Cl, Br or a hydrogen atom; A represents an oxygen or sulfur atom; and n is 1 or 2, and a carrier.

8. A method of controlling plant growth which comprises contacting a plant or part thereof with an effective amount of a compound selected from the group consisting of an N-(2,6-disubstituted 4-pyridyl)-N'-phenylurea compound of the formula:

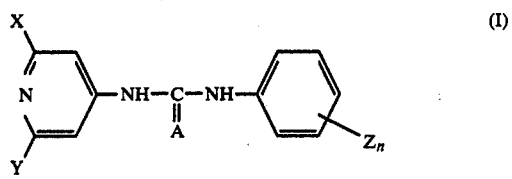

wherein X and Y, each of which may be the same or different, represents F, Cl, Br, CF$_3$, OR or SR wherein R represents a lower alkyl group; Z represents F, Cl, Br or a hydrogen atom; A represents an oxygen or sulfur atom; and n is 1 or 2.

* * * * *